(12) United States Patent
Kodama et al.

(10) Patent No.: US 6,489,612 B1
(45) Date of Patent: Dec. 3, 2002

(54) METHOD OF MEASURING FILM THICKNESS

(75) Inventors: Toshio Kodama, Chiba (JP); Yasuhiko Sugiyama, Chiba (JP); Toshiaki Fujii, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/701,606

(22) PCT Filed: Apr. 19, 2000

(86) PCT No.: PCT/JP00/02560
§ 371 (c)(1),
(2), (4) Date: Jan. 30, 2001

(87) PCT Pub. No.: WO00/65306
PCT Pub. Date: Nov. 2, 2000

(30) Foreign Application Priority Data

Apr. 21, 1999 (JP) .......................................... 11-113911

(51) Int. Cl.$^7$ ....................... H01J 37/28; H01J 37/256; G01N 23/00

(52) U.S. Cl. ....................................... 250/307; 250/309
(58) Field of Search .......................... 250/492.21, 309, 250/397

(56) References Cited

U.S. PATENT DOCUMENTS 5,055,696 A  * 10/1991  Haraichi et al. ......... 250/492.2
5,525,806 A  * 6/1996  Iwasaki et al. ........ 250/492.21
5,620,556 A  * 4/1997  Henck ........................... 438/8

FOREIGN PATENT DOCUMENTS

JP            363198348 A  *  8/1988

* cited by examiner

Primary Examiner—Bruce Anderson
(74) Attorney, Agent, or Firm—Adams & Wilks

(57) ABSTRACT

A thin film is etched by irradiating charged particles to a surface of the thin film. An etching time of the thin film is measured by observing a change in intensity of secondary charged particles emitted by etched portions of the thin film. A thickness of the thin film is calculated in accordance with the measured etching time.

24 Claims, 4 Drawing Sheets

541 : $SiO_2$   542 : Al

METHOD OF MEASURING FILM THICKNESS

BACKGROUND OF THE INVENTION

1. Field of the Invention

The present invention relates to a method for measuring film thickness of a thin film formed in, for example, a semiconductor manufacturing process.

2. Background Information

Conventionally, the following methods are known as methods for measuring the thickness of a thin film which is formed in a semiconductor manufacturing process:

(1) In the method shown in FIG. 5(A), the film thickness of a thin film is measured using an ellipsometer. In this measuring method, incident light IO irradiates a transparent thin film 512 placed on a substrate 511, and the intensity of the reflected light l1 is measured. At this time, the reflected light l1 is interference light between the light l11 reflected on the upper surface of the transparent thin film and the light l12 reflected on the lower surface thereof. Therefore, the intensity of the reflected light is maximized when a difference in an optical path length between the light l11 and the light l12 is a value an integer multiple of times larger than the irradiation light wavelength $\lambda$. Here, a difference in an optical path length L is obtained from $L=2d/\cos\theta$, wherein $\theta$ is an incident angle of the light I/O and D is a film thickness. Therefore, by obtaining an incident angle $\theta$ when $\lambda=L$ is held, the film thickness D of a transparent thin film can be obtained.

(2) According to the method shown in FIG. 5(B), a needle is placed on the surface of a thin film for measuring film thickness. In this measuring method, steps are formed between respective thin films 521, 521, which constitute a laminated film, using etching techniques. Then, a needle 522 is placed on the surfaces of the respective thin films 521, 521, and the positions of the needle 522 tip on the respective surfaces are detected for measurement of the film thicknesses of the respective thin films 521, 521.

(3) According to the method shown in FIG. 5(C), a film thickness is measured through observation of an etching cross section 531 formed on the thin film. In this method, an etching cross section 531 is initially formed on a laminated film by using, for example, a focusing ion beam device etc. Then, the cross section is observed by using a scanning electron microscope or a transmission electron microscope etc, so that a film thickness is measured.

(4) According to the method shown in FIG. 5(D), component analysis is applied to secondary ions while etching a laminated film. In the example. shown in FIG. 5(D), Si ions are discharged while etching a silicon thin film 541, and Al ions are discharged while etching an aluminum thin film 542. Therefore, etching times for the thin films 541, 542 can be known through component analysis applied to the secondary ions in parallel to the etching. Also, etching rates of the thin films 541, 542 are measured by using another method. Then, using the etching times and rates, the film thicknesses of the thin films 541, 542 are calculated.

The above described thin film measuring methods, however, have following drawbacks.

The method (1) suffers from the drawbacks that the film thickness of a thin film which is not photo transmissive cannot be measure, and that the film thickness of a thin film smaller than a light wavelength cannot be measured. For example, this method cannot measure the film thickness of an oxide film of about 10 nm, which as been recently used in practice for semiconductor devices.

The method (2) has a drawback that a larger burden is imposed on sample production due to very complicated etching processing. Therefore, it is substantially impossible to apply this method to a thin film having a complicated laminated structure.

The method (3) has a defect that the film thickness of a thin film smaller than the resolution of a scanning or transmission electron microscope cannot be measured. For example, as the limit of the resolution of a scanning electron microscope is 1 to 3 nm, the thickness of a thin film thinner than 1 to 3 nm cannot be measured using this method. This method has another drawback in that it requires an expensive measurement device when using a transmission electron microscope.

The method (4) has a drawback in that it requires an expensive measurement device as it requires component analysis.

The present invention has been conceived to overcome the above problems of the related art, and aims to provide a film thickness measuring method capable of measuring the film thickness of a very thin film and realized using an inexpensive measurement device.

SUMMARY OF THE INVENTION

According to the present invention, there is provided a film thickness measuring method using a focused ion beam device, comprising the steps of etching a thin film by irradiating charged particles to a surface of the thin film; measuring a change as time passes of strength of secondary charged particles discharged from the thin film during the step of etching; calculating an etching time of the thin film, using a point at which the strength changes quickly; and determining a film thickness of the thin film using the etching time.

A measurement method relative to the present invention can be realized using a very inexpensive device, compared to a case where an etching time is detected through component analysis, as an etching time is detected through observation of secondary charged particles. In addition, as a film thickness is determined using an etching time, resolution can be improved.

DETAILED DESCRIPTION OF THE PREFERRED EMBODIMENTS

In the following, preferred embodiments of the present invention will be described referring to the accompanying drawings. Note that the size and shape of and positional relationships between the respective structural components are shown schematized to an extent not hindering understanding of the invention. Also, conditions regarding values described below are merely examples.

First Embodiment

A thin film measuring method relative to a first preferred embodiment of the present invention will be described referring to FIG. 1 through FIG. 3.

Figure 1:
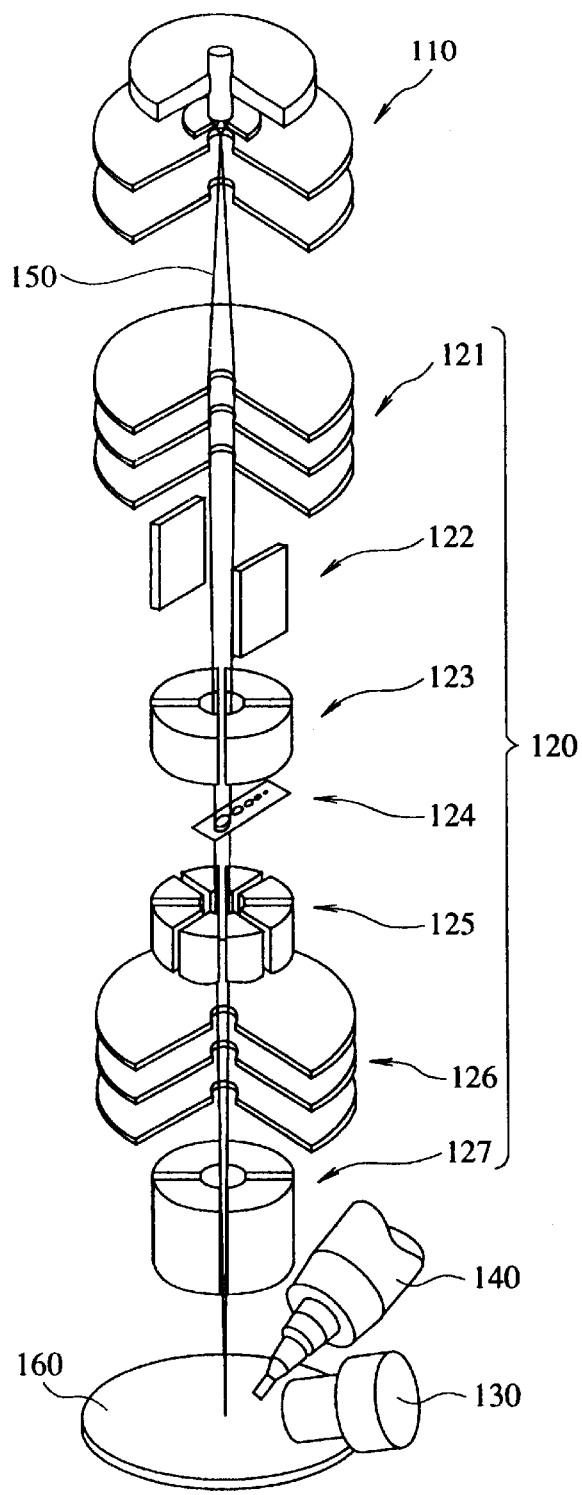
FIG. 1 is a conceptual view showing a structure of a focusing ion beam device relative to a preferred embodiment.

FIG. 1 is a diagram showing a structure of a focused ion beam device 100 used in this embodiment.

A liquid metal ion source 110 discharges, from the tip end thereof, metal ions such as gallium ions.

A capacitor lens 121 of an ion optical system 120 causes an electric field to deflect an ion beam 150 to form parallel beams.

A beam blanker 122 causes an electric field to deflect an ion beam 150 when irradiation of an ion beam 150 to a sample 160 is not desired.

An aligner 123 causes an electric field to adjust an axis of an ion beam 150.

A movable diaphragm 124 has a plurality of piercing holes with different diameters, and the diameter of the ion beam 150 is adjusted using any of the piercing holes. A piercing hole to be used is selected by using a driving mechanism (not shown).

A stigmeter 125 causes an electric field to adjust a beam shape such that an irradiation surface of the ion beam 150 becomes circular.

An object lens 126 adjusts a focal length through electric field strength such that the ion beam 150 is focused on the surface of the sample 160.

A deflector 127 scans an irradiation position of the ion beam 150, using an electric field.

A secondary electron detector 130 detects secondary electrons caused when the surface of the sample 160 is irradiated by the ion beam 150.

A gas gun 140 sprays stack or etching gas, supplied from a gas supplier mechanism (not shown) to the surface of the sample 160.

Figure 2:
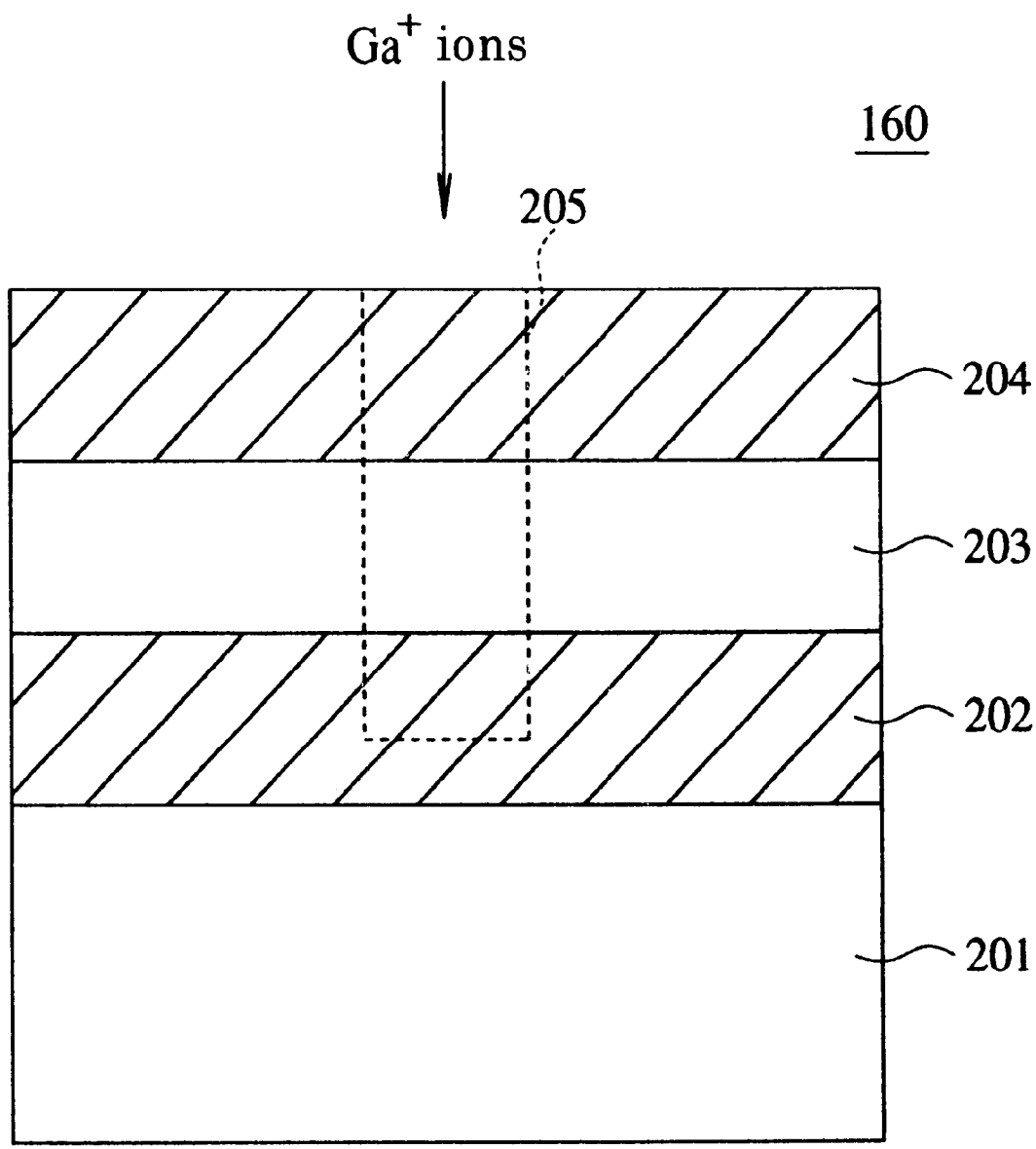
FIG. 2 is a cross section showing a laminated structure of a sample used in this embodiment.

FIG. 2 is a cross section showing an example of a sample used in a thin film measuring method according to this embodiment.

As shown in FIG. 2, the sample 160 comprises a thin film formed by sequentially forming an $SiO_2$ thin film layer 202, an Al thin film layer 203, and an $SiO_2$ thin film layer 204 on a substrate 201. Hereinafter, each of thin films 202–204 will be referred to as "thin film".

A method for measuring the film thickness of a sample 160 using a focused ion beam device 100 will next be described.

① A part to be etched of a sample 160 is determined, and the sample 160 is positioned such that the determined part is etched. Preferably, a part free from an IC, etc. is selected as a part to be etched. For example, a part close to an alignment mark of the sample 160 may be selected as a part to be etched.

② Then, discharging of Ga+ ions from a liquid metal ion source 110 is started, and spraying of etching gas from a gas gun 140 is also started whereby etching processing is started. With this etching processing, an etching hole 205 is formed on the sample 160 at a predetermined etching rate (see FIG. 2).

Here, this is little restriction placed on the kind of metal ion that can be used, though ions having little influence on the sample 160 are preferred. For example, Ga+ ions can be used.

The current of the ion beam. 150 is set such that its dose amount in a unit time is constant, though it may be continuous or intermittent.

An electric current value and an acceleration voltage of the ion beam 150 are set such that etching processing is carried out at a predetermined etching rate. An etching rate employed in measurement of this embodiment is not particularly restricted. With a large etching rate, film thick measurement can be completed in a short time even when thin films 202 to 204 are thick. On the other hand, with a small etching rate, film thickness measurement can be achieved with improved accuracy as a change, as time passes, of an amount of secondary electron discharge can be observed in detail even when the thin films 202 to 204 are very thin.

An incident angle of the ion beam 150 with respect to the sample 160 is not particularly restricted, and may generally be vertical.

A diameter of the ion beam 150 is not particularly restricted. However, with too large a beam diameter, an IC formation area, etc. of the sample 160 may possibly be destroyed. Therefore, the beam diameter is desired to be sufficiently small with respect to a pattern size of an IC, etc.

The diameter of an etching hole 205 is also not particularly restricted in this embodiment. However, with a larger beam diameter, measurement accuracy can be improved as secondary electrons, generated in the etching hole 205, can more easily be discharged to the outside of the hole. Therefore, the diameter of the etching hole 205 may be adjusted by adjusting the ion beam 150.

③ In parallel with the above described etching processing (step 2), secondary electron detection is also applied. When etching using a focused ion beam device 100, secondary electrons are generated in a part to be etched. The secondary electrons generated are partly discharged from the etching hole 205, reaching the secondary electron detector 130. The secondary electron detector 130 observes a change as time passes of the strength of the secondary electrons.

Figure 3:
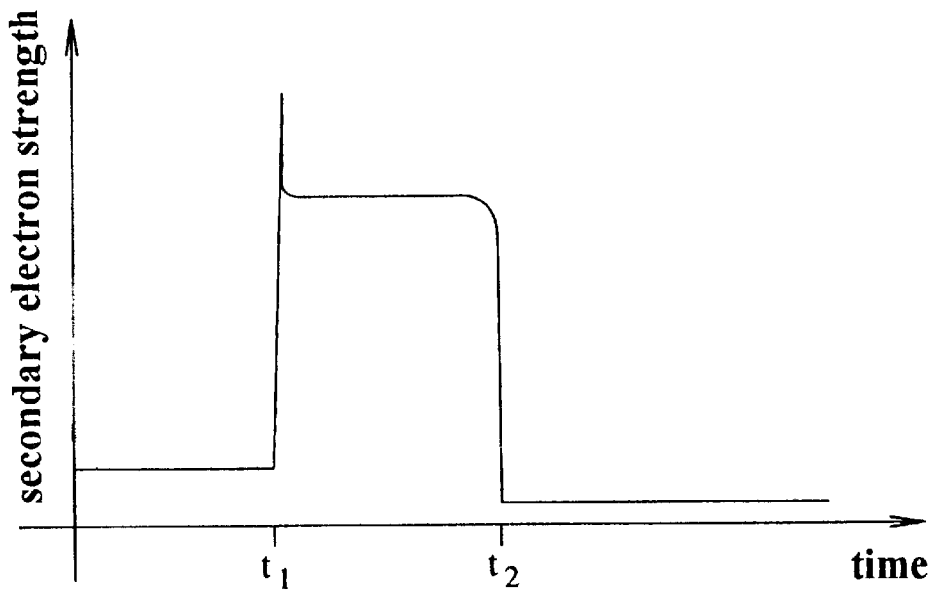
FIG. 3 is a graph showing a change as time passes of secondary electronic strength observed in a first preferred embodiment.

FIG. 3 is a graph showing a change as time passes of the strength of secondary electrons, with the horizontal axis indicating time and the vertical axis indicating the strength of secondary electrons (a standard value).

In FIG. 3, time t1 is a time at which the etching hole 205 (see FIG. 2) reaches the surface of the Al thin film 203. That is, at time t1, etching is completed with the $SiO_2$ thin film 204, and started with the Al thin film 203. As known from FIG. 3, the strength of secondary electrons is much larger while etching the Al thin film 203 than that while etching the $SiO_2$ thin film 204. Therefore, an etching end time t1 with respect to the $SiO_2$ thin film 204 can be known from a quick or abrupt increase of the strength of secondary electrons.

In FIG. 3, time t2 is a time at which the etching hole 205 reaches the surface of the $SiO_2$ thin film 202. That is, at time t2, etching is completed with the Al thin film 203, and started with the $SiO_2$ thin film 202. As described above, the strength of secondary electrons is smaller while etching the $SiO_2$ thin film 204 than that while etching the Al thin film 203. Therefore, an etching end time t2 with respect to the Al thin film 203 can be known from a quick or abrupt decrease of the strength of secondary electrons.

Times t1, t2 can be detected through value execution processing using output data from the secondary electron detector 130. That is, by detecting a point at which the strength of secondary electrons is changed, through this execution processing, times t1, t2 can be detected.

Also, times t1, t2 can be detected by using a high pass filter. That is, an output signal from the secondary electron detector 130 is input to a high pass filter, and times at which a peak waveform is output from the filter may be determined as times t1, t2.

④ Next, a time spent for etching the $SiO_2$ thin film 204 and that for etching the Al thin film 203 are calculated using times t1, t2. As known from FIG. 3, an etching time for the $SiO_2$ nthin film 204 is a difference between an etching start time and time t1, i.e., t1. Also, an etching time for the Al thin film 203 is a difference between time t1 and time t2, i.e., t2−t1.

Then, the film thicknesses of the thin films 204, 203 are calculated through multiplication of these etching times and rates.

Here, an etching rate can be obtained, for example, through measurement of an enticing time of a sample with a known thickness in a manner similar to the above described processes ① through ③.

Note that whether the thin films 203, 204 are good/no good may be determined using an etching time, rather than calculating a film thickness value thereof. That is, etching times for good (i.e., a semiconductor device guaranteed for normal operation) thin films 203, 204 are measured in advance to be used as comparison values, and etching times, obtained through the above step (4), are compared with the comparison values, whereby whether or not the film thickness is within a tolerance range can be determined.

⑤ Thereafter, the etching hole 205 may be refilled, if necessary, to complete film thickness measurement.

As described above, according to this embodiment, film thickness can be measured using a very inexpensive device as an etching time is detected through observation of secondary electrons, compared to a case where an etching time is detected through component analysis (see related art (4)). In addition, as a conventional focusing ion beam device can be used intact for film thickness measurement, a device which is inexpensive also in this view can be used.

Also, a film thickness measurement method according to this embodiment can measure the film thickness of a film which is not photo transmissive, as well as the film thickness of a film smaller than a light wavelength or resolution of a scanning or transmission electron microscope.

Further, the film thickness of a thin film can be measured in a short time as formation of steps in a sample is unnecessary.

Second Embodiment

Next, a thin film measuring method in a second preferred embodiment of the present invention will be described referring to FIG. 4.

A structure of a focused ion beam device used in this embodiment is substantially identical to that of the device 100 used in the first preferred embodiment (see FIG. 1), which, however, is different in that the device in the second embodiment uses a secondary ion detector (not shown) in the place of a secondary electron detector 130.

A sample similar to the sample 160 (see FIG. 2) used in the first preferred embodiment is used as a sample for film thickness measurement.

In the following, a film thickness measurement method according to this embodiment will be described.

① Similar to the first preferred embodiment, a part to be etched of a sample 160 is determined, and the sample 160 is positioned such that the part is etched.

② Further, similar to the first preferred embodiment, Ga+ ions discharging and etching gas spraying are started to thereby start formation of an etching hole 205 (see FIG. 2).

Note that the type of usable metal ions, a current value, an acceleration voltage, an incident angle, and a beam diameter of an ion beam 150 can be determined similar to the first preferred embodiment.

③ In parallel to the above described etching processing (step 2), secondary ion detection is carried out. When etching using a focused ion beam device 100, secondary ions are generated in the part to be etched. The secondary ions generated are partially discharged from the etching hole 205, and reach a secondary ion detector. The secondary ion detector observes a change as time passes of the strength of secondary ions.

Figure 4:
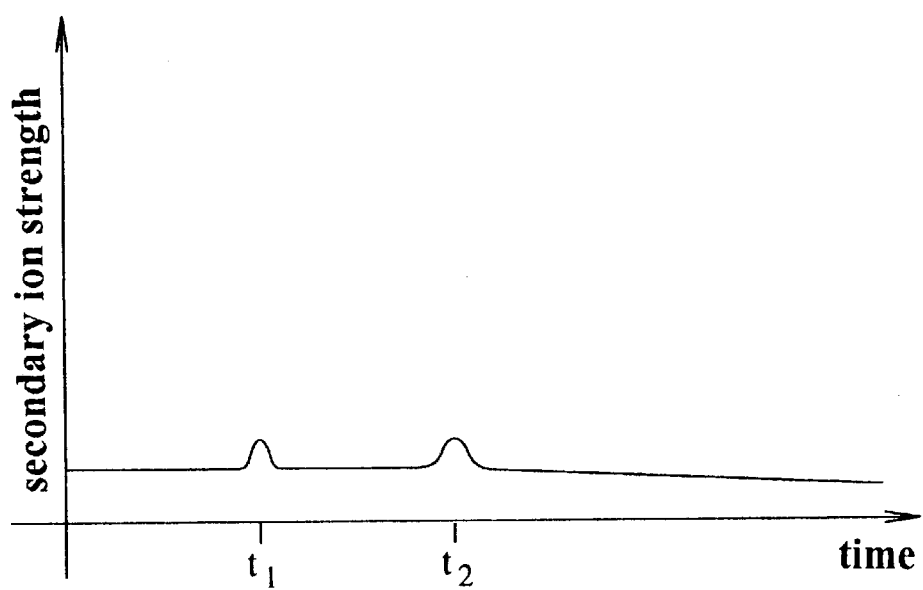
FIG. 4 is a graph showing a change as time passes of secondary ion strength observed in a second preferred embodiment.
Figure 5A:
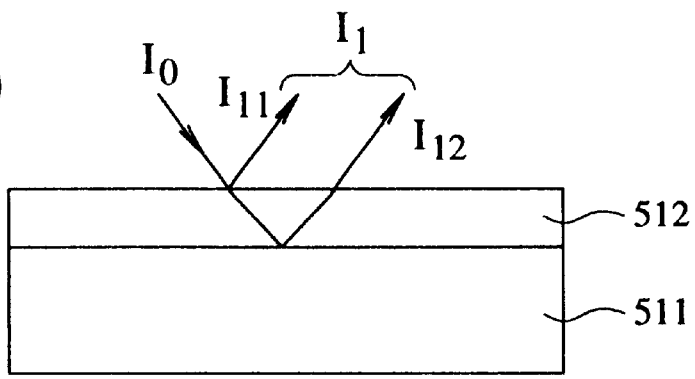
FIGS. 5(A) through (D) are conceptual views explaining a conventional film thickness measuring method.
Figure 5B:
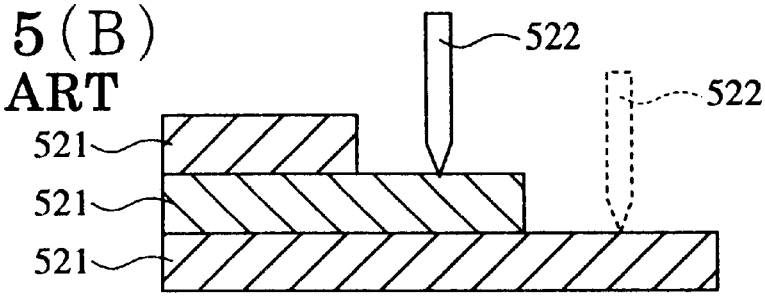
Figure 5C:
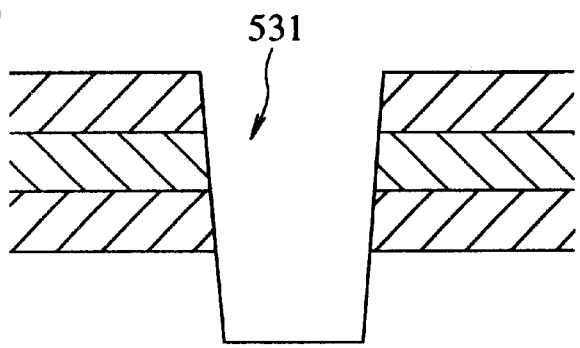
Figure 5D:
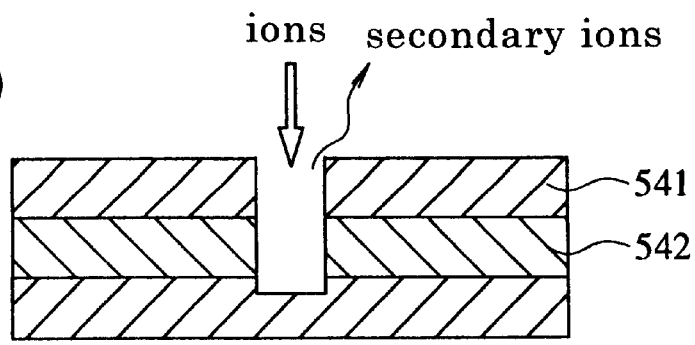

FIG. 4 is a graph showing a change as time passes of the strength of secondary ions, wherein the horizontal axis shows time and the vertical axis shows secondary ion strength (a regular value).

In FIG. 4, time t1 is a time at which the etching hole 205 reaches the surface of the Al thin film 203. That is, at time T1, etching is completed with the $SiO_2$ thin film 204, and started with the Al thin film 203. Also, in FIG. 4, at time t2, the etching hole 205 reaches the surface of the $SiO_2$ thin film 202. That is, at time t2, etching is completed for the Al thin film 203, and started for the $SiO_2$ thin film 202.

As known from FIG. 4, the strength of secondary ions increases when etching a part close to the boundary between the $SiO_2$ thin film 204 and the Al thin film 203 and a part close to the boundary between the Al thin film 203 and the $SiO_2$ thin film 202. Therefore, times t1, t2 can be known by detecting an etching temporal increase of the strength of secondary ions.

Similar to the first preferred embodiment, times t1, t2 can be detected, for example, by giving value execution processing to an output signal from the secondary ion detector, or filtering the output signal using a high pass filter.

④ Next, similar to the first preferred embodiment, an etching time for the $SiO_2$ thin film 204 and that for the Al thin film 203 are calculated using times t1, t2, and the film thicknesses of the thin films 204, 203 are calculated based on these etching times and rates.

An etching rate can be obtained in a method similar to that in the first preferred embodiment. This embodiment is similar to the first preferred embodiment also in that thin films 203, 204 can be determined to be good/no good, rather than calculating a value of film thickness.

⑤ Thereafter, the etching hole 205 is refilled, if necessary, to complete film thickness measurement.

As described above, according to this embodiment, an etching time can be detected through observation of secondary ions.

With the above, similar to the first preferred embodiment, film thickness measurement can be achieved using a very inexpensive device, compared to a case where an etching time is detected through component analysis.

In addition, this embodiment is similar to the first preferred embodiment in that a conventional focusing ion beam device can be used intact, that the thickness of a film which is not photo transmissive can be measured, as well as the thickness. of a thin film smaller than a light waveform or the resolution of a scanning or transmission electron microscope, and that etching processing is very easy.

INDUSTRIAL APPLICABILITY

As described in detail in the above, according to the present invention, there can be provided a film thickness measuring method capable of measuring a film thickness of a very thin film, and realized using an inexpensive measuring device.

What is claimed is:

1. A film thickness measuring method, comprising the steps of:

etching a thin film by irradiating charged particles to a surface of the thin film;

measuring as a function of time a change of a strength of secondary charged particles discharged from the thin film during the etching step;

calculating an etching time of the thin film in accordance with a point at which the measured strength changes abruptly; and determining a thickness of the thin film in accordance with the calculated etching time.

2. A film thickness measuring method according to claim 1; wherein the thin film comprises a plurality of laminated thin film layers; and wherein the etching step comprises continuously etching two or more of the thin film layers.

3. A film thickness measuring method according to claim 2; wherein the calculating step comprises determining an etching time of an uppermost one of the thin film layers from the start of etching to an initial abrupt change of the strength of the secondary charged particles, and for determining an etching time of a second or subsequent one of the thin film layers from the initial abrupt change of the strength to a next abrupt change of the strength of the secondary charged particles.

4. A film thickness measuring method according to claim 3; wherein the determining step comprises calculating the film thickness as a function of etching time and etching rate.

5. A film thickness measuring method according to claim 4; wherein the measuring step comprises measuring the strength of secondary electrons or secondary ions as the strength of the secondary charged particles.

6. A film thickness measuring method according to claim 3; wherein the determining step includes judging whether the thickness of the thin film is within a desired tolerance range by comparing the etching time with preselected etching time comparison values.

7. A film thickness measuring method according to claim 5; wherein the measuring step comprises measuring the strength of secondary electrons or secondary ions as the strength of the secondary charged particles.

8. A film thickness measuring method according to claim 3; wherein the measuring step comprises measuring the strength of secondary electrons or secondary ions as the strength of the secondary charged particles.

9. A film thickness measuring method according to claim 2; wherein the determining step comprises calculating the film thickness as a function of etching time and etching rate.

10. A film thickness measuring method according to claim 2; wherein the determining step includes judging whether the thickness of the thin film is within a desired tolerance range by comparing the etching time with preselected etching time comparison values.

11. A film thickness measuring method according to claim 2; wherein the measuring step comprises measuring the strength of secondary electrons or secondary ions as the strength of the secondary charged particles.

12. A film thickness measuring method according to claim 1; wherein the determining step comprises calculating the film thickness as a function of etching time and etching rate.

13. A film thickness measuring method according to claim 1; wherein the determining step includes judging whether the thickness of the thin film is within a desired tolerance range by comparing the etching time with preselected etching time comparison values.

14. A film thickness measuring method according to claim 1; wherein the measuring step comprises measuring the strength of secondary electrons or secondary ions as the strength of the secondary charged particles.

15. A film thickness measuring method comprising the steps of: providing a thin film; etching the thin film by irradiating charged particles to a surface of the thin film; measuring an etching time of the thin film by observing a change in intensity of secondary charged particles emitted by etched portions of the thin film; and calculating a thickness of the thin film in accordance with the measured etching time.

16. A film thickness measuring method according to claim 15; wherein the thin film comprises a plurality of laminated thin film layers; and wherein the etching step comprises continuously etching at least two of the thin film layers.

17. A film thickness measuring method according to claim 15; wherein the etching step comprises etching the thin film by irradiating charged particles to a surface of the thin film using a focused ion beam device.

18. A film thickness measuring method according to claim 15; wherein the etching step comprises irradiating the charged particles to form a hole in the surface of the thin film.

19. A film thickness measuring method according to claim 18; wherein the thin film comprises a plurality of laminated thin film layers; and wherein the etching step comprises forming the hole to extend through two of the thin film layers.

20. A film thickness measuring method according to claim 18; wherein the thin film comprises three laminated thin film layers; and wherein the etching step comprises forming the hole to extend through two of the thin film layers and into the third thin film layer.

21. A film thickness measuring method according to claim 15; wherein the secondary charged particles emitted by the etched portions of the thin film comprise secondary electrons.

22. A film thickness measuring method according to claim 15; wherein the secondary charged particles emitted by the etched portions of the thin film comprise secondary ions.

23. A film thickness measuring method comprising the steps of: providing a sample comprised of a plurality of laminated thin film layers; etching the sample by irradiating charged particles to a surface of the sample to form a hole extending through at least one of the thin film layers in a thickness direction of the sample; measuring an etching time of the sample by observing a change in intensity of secondary charged particles emitted by etched portions of the thin film; and calculating a thickness of the sample in accordance with the measured etching time.

24. A film thickness measuring method according to claim 23; wherein the etching step comprises etching the sample by irradiating charged particles to a surface of the sample using a focused ion beam device.

* * * * *